United States Patent
Schillinger et al.

(12) 
(10) Patent No.: US 6,376,754 B1
(45) Date of Patent: *Apr. 23, 2002

(54) PLANTS HAVING RESISTANCE TO MULTIPLE HERBICIDES AND ITS USE

(75) Inventors: John A. Schillinger, Kalamazoo, MI (US); Alan K. Walker, Janesville, WI (US); Joseph R. Byrum, W. Des Moines, IA (US)

(73) Assignee: Asgrow Seed Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/813,788

(22) Filed: Mar. 7, 1997

(51) Int. Cl.[7] .............................. A01H 5/00; C12N 5/04; C12N 15/82
(52) U.S. Cl. ....................... 800/312; 800/260; 800/298; 800/278; 800/300; 435/415; 435/419
(58) Field of Search .................................. 800/312, 260, 800/298, 278, 300; 504/214, 215, 247, 253; 435/419, 415

(56) References Cited

U.S. PATENT DOCUMENTS

| | | | | |
|---|---|---|---|---|
| 4,761,373 A | | 8/1988 | Anderson et al. | |
| 5,084,082 A | * | 1/1992 | Sebastian | ...................... 71/90 |
| 5,416,011 A | | 5/1995 | Hinchee et al. | |
| 5,463,175 A | | 10/1995 | Barry et al. | |
| 5,554,798 A | | 9/1996 | Lundquist et al. | |
| 5,576,477 A | | 11/1996 | Matson | |
| 5,602,319 A | * | 2/1997 | Rhodes et al. | .............. 800/200 |
| 5,710,368 A | * | 1/1998 | Rhodes | ........................ 800/200 |

OTHER PUBLICATIONS

Padgette et al, Crop Sci 35:1451–1461, Sep. 1995.*

* cited by examiner

*Primary Examiner*—Elizabeth F. McElwain
(74) *Attorney, Agent, or Firm*—Rothwell, Figg, Ernst & Manbeck

(57) ABSTRACT

This invention relates to a plant, seed, variety, inbred and hybrid. More specifically, the invention relates to plant having resistance to at least two herbicides. The invention also relates to methods of producing a hybrid plant and methods of producing a plant having resistance to at least two herbicides.

12 Claims, No Drawings

PLANTS HAVING RESISTANCE TO MULTIPLE HERBICIDES AND ITS USE

The present invention relates to a seed, a plant, a variety, an inbred, and a hybrid which contain a level of resistance to more than one herbicide. Such plants have advantages over plants having a single gene for herbicide resistance, especially with respect to prevention of resistance development in the target weed plants.

BACKGROUND OF INVENTION

The features of a commercially competitive plant varieties generally include more than high yield with excellent standability. While yield is the single most critical input which affects the crop producer's profit, producers expect consistency of yield from year to year, disease resistance, other value-added traits, and—more recently—herbicide resistance. The addition of herbicide resistance has created both opportunities as well as tremendous challenges in production agriculture.

Historically, herbicide treatments have been an integral part of modern agriculture because they provide cost-effective increases in agricultural productivity. Increased yields result from reduced weed competition for water, light, and nutrients. In addition, crop quality often improves in the absence of contaminating weed seeds. Herbicides can also aid soil conservation efforts through no-till agricultural practices, wherein herbicides rather than tillage are used to reduce weed populations prior to planting.

Herbicides generally give more consistent weed control compared to tillage in many environments. Consequently, there is increasing use of both non-selective herbicides for weed control prior to crop establishment and selective herbicides for crop weed control while a crop is growing. Non-selective herbicides kill or inhibit the growth of all actively growing plant material. Selective herbicides are those herbicides generally used for the suppression of growth of certain plant species (usually weeds), while leaving another species (usually a crop) unaffected. In North America and many other countries, these herbicides have benefitted the farmer by enabling the earlier planting of short-season crops, and by improving weed control in many cropping systems.

Herbicide development programs have always assessed the crop safety of a given herbicide in a weed control system, so that no crop yield reduction results from herbicide application. In fact, crop safety has been a focus of chemical herbicide discovery and plant breeding for the last 30 years, and thousands of chemical analogues have been screened to allow identification of herbicides that control target weeds and are safe to crops minimizing yield loss due to chemical stress. Nevertheless, while several classes of herbicides possess a broad spectrum of efficacy, many of the herbicides lack selectivity and severely injure or kill crop plants at the application rates required for effective weed control.

Examples of widely used herbicides are chlorimuron and thifensulfuron, which belong to the sulfonylurea class. They inhibit the plant enzyme acetolactate synthase (also called ALS), and soybeans which are resistant to these herbicides are referred to as STS (also called sulfonylurea tolerant) soybeans. These herbicides are the active ingredients in Classic and Pinnacle, respectively, and are registered for control of broadleaf weeds in soybeans as described in Weed Science Society of America, Herbicide Handbook, 7th edition (1994). While chlorimuron and thifensulfuron are registered for use in non-STS soybeans, they can cause significant crop injury, especially if applied post-emergence as described in Fielding and Stoller, Weed Technol. 4:264–271 (1990); Fielding and Stoller, Weed Sci. 38:172–178 (1990); Newsom and Shaw, Weed Sci. 42:608–613 (1994); and Ahrens, Weed Technol. 4:524–528 (1990). Factors which influence the extent of herbicide injury are physiological stresses from poor seed quality, delayed emergence in cold and wet soils, seedling diseases, etc.; soil pH and climatic conditions (i.e. temperature and humidity) when applications are made; and injury from prior applications of chemicals (e.g. insecticides and other herbicides).

When these herbicides are combined, either intentionally or unintentionally, positive and negative interactions can result. Chlorimuron and thifensulfuron are sold pre-mixed at elevated rates under the trade names Synchrony and Reliance, and act cooperatively to broaden the spectrum of weeds controlled. On the other hand, thifensulfuron interacts synergistically with imazethapyr (the active ingredient in the herbicide Pursuit) at normal use rates to severely injure non-STS soybeans; this combination causes less injury to STS soybeans but injury can exceed 20% which is commercially unacceptable and is discussed in Simpson and Stoller, Weed Technol. 9:582–586 (1995).

Glyphosate, which belongs to a different class of herbicide and is the active ingredient in both Roundup (also called RR) and Roundup Ultra, complements activity of the other herbicides (e.g. 2,4-D and dicamba). In some cases, glyphosate interacts synergistically with these other herbicides when they are applied in combination, as shown in Moshier, Weed Sci. 28:722–724 (1980) and Flint and Barrett, Weed Sci. 37:12–18 (1989). Tank mixing Classic at 0.5 oz/A or Pinnacle at 0.125 oz/A with Roundup at 16 fl oz/A increases control of broadleaf weeds but, in the case of Pinnacle, injury of Roundup Ready soybean is greater with the combination than with Roundup alone as discussed in Lich and Renner, Proc. NCWSS 50:124 (1995). Combination of Roundup Ultra with Synchrony (premix of chlorimuron plus thifensulfuron at elevated rates) effectively controls a broad spectrum of weeds.

Combining glyphosate with Synchrony or Reliance has the potential of increasing the spectrum of weeds (e.g. annual and perennial grasses, smartweeds, nightshade, pigweed spp., morningglory spp., etc.) that are controlled. Consequently, combining or "stacking" a level of resistance to both glyphosate and ALS in soybeans will allow these herbicide combinations to be used for effective weed control without crop injury.

With the development of chemical crop protection and the increasing availability of effective selective herbicides, monocultures of crops have become common. This has led to repeated application of the same or similar herbicides to these crops. More recently, in conservation or zero-tillage crop establishment systems, cultivation for weed control has largely been replaced by the use of selective and non-selective herbicides. Thus, two prevailing conditions are present in these cropping systems: (i) the frequent use of a limited range of effective herbicides and (ii) reliance upon these herbicides to the exclusion of other forms of weed control. Where these conditions prevail, herbicide-resistant weeds will increase in frequency (i.e. evolve) if there is heritable variability in response to herbicide application in weed populations and selective mortality from the herbicides.

Given the existence of genetic variation, the rate of evolution will be determined by the mode of inheritance of resistance traits, together with the intensity of selection. The evolution of resistance under persistent applications of herbicide may be considered as an example of recurrent selection in which there is a progressive, and sometimes rapid, shift in average fitness of populations of weeds exposed to herbicide. Once established, gene flow via seed distribution has probably contributed to the spread of resistant weeds. A major determinant in the selection of herbicide-resistant biotypes is the effective selection intensity that differentiates resistant individuals (more fit) from susceptible one (less fit) in the face of selection (the application of herbicide).

There are two ways in which resistance traits may arise within a weed population. A major gene, or genes may be present at low frequency, or mutate, so that selection acts to change a population which is initially susceptible. Alternatively, recurrent selection may act on continuous (quantitative) variation and achieve a progressive increase in average resistance from generation to generation, with changes in gene frequency at many loci conferring resistance.

Genetic variation can arise de novo by mutation (or recombination) or be preexisting. We can thus distinguish two situations with regard of genetic variation for herbicide resistance in nonselected populations: (1) factors affecting the acquisition of resistance by novel mutation and (2) factors affecting the probability of preexisting variation for resistance.

One of the most significant occurrences in herbicide resistance has been the advent of weeds resistant to herbicides that inhibit acetolactate synthase (ALS). This is because ALS inhibitor herbicides have become extremely important new tools in agricultural production, and any development which might limit their utility is regarded as serious. The use of two major classes of ALS inhibitor herbicides alone—sulfonylureas and imidazolinones—has grown to a 1991 market value of approximately $1.3 billion. This popularity is due to relatively low use rates, sound environmental properties, low mammalian toxicity, wide crop selectivity, and high efficacy. Five years after the initial use of an ALS inhibitor herbicide, the first resistant weeds appeared, and their incidence has steadily increased both in number of sites and species. A large factor in the appearance of resistance is the high selection pressure imposed by ALS inhibitor herbicides on very sensitive weed species. The occurrence of target site, ALS inhibitor resistance as most frequently resulted form the selection pressure associated with long residual herbicides and monoculture or near monoculture conditions.

When weed populations become sufficiently enriched with weed resistant biotypes such that they cannot be controlled by the usual rate of herbicide and the weed burden causes, or threatens, loss of crop production, then changes in weed control techniques must be implemented. However, in order to minimize the need for remedial measure after resistance develops, more complex strategies for weed control are required in order to delay or prevent the evolution of resistance. Ideally, these strategies should include the use of crop rotations, herbicide mixtures or rotations, tillage, and integrated pest management techniques where possible.

For a number of technical and practical reasons, resistance to herbicides in agronomically important crops was among the first traits to which recombinant DNA technology and novel genetic approaches were applied. The advent of Roundup Ready (RR) Soybeans which have a level of resistance to glyphosate, and Liberty Link (LL) Soybeans which have a level of resistance to the herbicide glufosinate has provided new and exciting opportunities in agriculture. This technology has allowed developers of soybean varieties to build herbicide selectivity and true crop safety mechanisms into soybean. This approach thus has expanded the utility of proven, previously non-selective, broad spectrum herbicides. These herbicide resistant crops enable improved weed control and greater flexibility in herbicide application, resulting in better production systems. New herbicide resistance traits can be developed as components of new weed control systems featuring herbicides with the beneficial environmental characteristics needed to meet current and future rigorous demands on active ingredients.

Unfortunately economic and/or governmental regulations often limit the implementation of these strategies. For example the predominant use of one herbicide in monoculture as practiced in the northern Great Plains is among the least appropriate from a weed resistance management perspective. Many agronomic practices are between the extremes of monoculture and complex rotations, and include both monoculture with herbicides having several modes of action, and rotational culture with herbicides having single modes of action. Even these more integrated markets, however, are tending towards less herbicide diversity and an increased weed resistance potential due to the introduction of new herbicides with the same chemistry and new soybean herbicide resistant crops (HRC).

SUMMARY OF THE INVENTION

The present invention relates to a seed, a plant, a variety, an inbred, a hybrid and the progeny derived from them.

More specifically, the invention relates to a plant having resistance to at least two herbicides. The invention further relates to a plant having resistance to at least two herbicides and having a commercially acceptable grain yield. The invention further relates to a method of producing a hybrid plant.

In another aspect, the invention relates to a method of producing a hybrid soybean seed. The present invention further relates to a soybean plant having resistance to at least two herbicides. The invention further relates to a soybean plant having resistance to at least two herbicides and having a commercially acceptable grain yield.

The invention further relates to a soybean plant having a level of resistance to glyphosate or Roundup™ herbicide and to sulfonylurea or STS™ herbicide.

The invention further relates to a soybean plant having a level of resistance to glufosinate or Liberty™ herbicide and sulfonylurea or STS™ herbicides.

The invention further relates to a soybean plant having a level of resistance to glyphosate and to glufosinate herbicides.

The invention further relates to a soybean plant having a level of resistance to glyphosate or Roundup™, glufosinate or Liberty™ and sulfonylurea or STS™ herbicide.

The present invention further relates to a soybean plant having a level of resistance to at least two herbicides, wherein said herbicides are selected from the group consisting of atrazine, ALS inhibitor, glyphosate, glufosinate and isoxoflutole.

The present invention further relates to a method of producing a soybean plant having resistance to at least two herbicides.

DETAILED DESCRIPTION OF INVENTION

To provide an understanding of several of the terms used in the specification and claims, the following definitions are provided:

Agronomically acceptable injury—As used herein the term agronomically acceptable injury means any herbicide injury resulting in a less than 10 percent reduction in yield when compared to the same variety having no herbicidal injury.

Agronomically Fit—As used herein, the term agronomically fit means a genotype that has the culmination of many distinguishable traits such as emergence, vigor, vegetative vigor, disease resistance, seed set, standability and threshability which allows a producer to harvest a product of commercial significance.

ALS Inhibitor—As used herein, the ALS inhibitor means any herbicidally effective form of sulfonylureas, triazolopyrimidine sulfonamides, imidazolinones or heteroaryl ethers including any salt thereof or other related compounds or derivatives.

Atrazine—As used herein, the term atrazine means any herbicidally effective form of triazine, including 6-40 N-ethyl-N'-(1 methylethyl)-1,3,5 triazine-2,4 diamine, and including any salt thereof or other related compounds or derivatives.

Base Population—As used herein, the term base population means the development of segregating populations during inbreeding until the desired lelvel of homozygosity is achieved. Selection of plants or parts of plants are either random or nonrandom and advanced to the next generation. The lines derived from the plants are evaluated for the characteristics of interest.

Commercially acceptable—The term commercially acceptable means a soybean variety having a grain yield of greater than 35 bushels per acre over at least two years and 10 environments.

Glufosinate—As used herein, the term glufosinate means any herbicidally effective form of phosphinothricin, including any salt thereof or other related compounds or derivatives.

Glyphosate—As used herein, the term glyphosate means any herbicidally effective form of N-phosphonomethylglycine including any salt thereof or other related compounds or derivatives or any other 5-enolpyrunyl 3-shilkimate phosphate synthase inhibitor.

Herbicide Resistance—The term herbicide resistance means the ability to survive with agronomically acceptable injury, a concentration of herbicide that is normally lethal or extremely injurious to individual plants of a given species.

Isoxaflutole—As used herein, the term isoxaflutole means any herbicidally effective form of 5-cyclopropyl-4 (methane sulphonyl 1-4-thifluoromethylbenzoyl), isoxazole or other related compounds or derivatives.

Stacking—As used herein, the term stacking means genetically combining multiple herbicide resistant traits into a commercially acceptable cultivar using conventional plant breeding and/or genetic engineering methods.

The advent of genetic engineering has provided agricultural industry with soybeans that are resistant to glyphosate or glufosinate or sulfonylureas. Prior to the instant invention, a soybean variety has never been developed having more than one herbicide resistance trait combined into one soybean genotype. These herbicide genes have not previously been stacked in any commercial or wild type soybean. Having multiple herbicide resistant genes in one soybean variety substantially expands the utility to use proven, previously nonselective, broad spectrum herbicides. Herbicide Resistant Crops, also called HRC, provide improved weed control and greater flexibility in herbicide application resulting in better production systems. The use of herbicides with alternate modes of action in a given weed management system offers advantages in extending the lives of current programs, such as in weed resistance management. Also, new weed control systems featuring herbicides with beneficial environmental characteristics are needed to meet current and future rigorous demands on active ingredients.

The likelihood of target site resistance developing in a population to a mixture of herbicides is the mathematical product of the frequency of any genes conferring resistance to the mixture components. Mixtures can, therefore, be an effective tool in weed resistance management of autogamous species, because individual plants bearing multiple mutations will be extremely rare and gene flow between surviving plants is low.

Since in the instant invention the new herbicide resistance genes are introduced into varieties with acceptable genetic backgrounds (i.e. with high yield, excellent standability, and multiple disease and pest resistance), the resistances can be rapidly combined, developed into commercially acceptable cultivars, and made available to the farmer. Thus, these cultivars with stacked resistance traits can be extremely useful in agriculture.

All crop species are grown for the purpose of harvesting some product of commercial significance. Enhancement of productivity or yield of that product is a major goal of most plant breeding programs. The highest priority in most soybean cultivar development programs is increasing seed yield. Seed yield is a quantitative character controlled by many genes and strongly influenced by the environment. The heritability of yield is the lowest and the most variable of the major agronomic traits considered in cultivar development, with heritability estimates ranging from 3 to 58%. Yield is an example of a quantitative character that breeders attempt to improve beyond the level of that present in current cultivars. Disease resistance is required in most cases to protect the yield potential of a cultivar.

It is a difficult challenge to incorporate one herbicide resistant or tolerant trait into high yielding cultivars. The difficulty of obtaining a commercially acceptable variety is increased by several orders of magnitude if a breeder attempts to combine two herbicide resistance or tolerance traits into one cultivar. For a plant breeder to find a cultivar with sufficient merit (e.g. high yielding) to be increased and commercially distributed, it is necessary to make many crosses and grow thousands of experimental genotypes. The evaluation of so many genotypes is a huge task, and consumes an enormous amount of the plant breeder's time and budget. In some instances, it can take a decade or more from the time the original cross is made to the time when a commercially viable genotype is identified.

The effectiveness of selecting for genotypes with the traits of interest (e.g., high yield, disease resistance, herbicide resistance) in a breeding program will depend upon: 1) the extent to which the variability in the traits of interest of individual plants in a population is the result of genetic factors and is thus transmitted to the progenies of the selected genotypes; and 2) how much the variability in the traits of interest (yield, disease traits, herbicide resistance) among the plants is due to the environment in which the different genotypes are growing. The inheritance of traits ranges from control by one major gene whose expression is not influenced by the environment (i.e., qualitative characters) to control by many genes whose effects are greatly influenced by the environment (i.e., quantitative characters). Breeding for quantitative traits is further characterized by the fact that: 1) the differences resulting from the effect of each gene are small, making it difficult or impossible to identify them individually; 2) the number of genes contributing to a character is large, so that distinct segregation ratios are seldom if ever obtained; and 3) the effects of the genes may be expressed in different ways based on environmental variation. Therefore, the accurate identification of transgressive segregants or superior genotypes with the traits of interest is extremely difficult and its success is dependent on the plant breeder's ability to minimize the environmental variation affecting the expression of the quantitative character in the population. The likelihood of identifying a transgressive segregant is greatly reduced as the number of traits combined into one genotype is increased. For example, if a cross is made between cultivars differing in three complex characters, such as yield, disease resistance and herbicide resistance, it is extremely difficult to recover simultaneously by recombination the maximum number of favorable genes for each of the three characters into one genotype. Consequently, all the breeder can generally hope for is to obtain a favorable assortment of genes for the first complex character combined with a favorable assortment of genes for the second character into one genotype in addition to a herbicide resistant gene.

The methods used in cultivar development programs and their probability of success are dependent on the number of characters to be improved simultaneously, such as, seed yield, disease resistance, and herbicide resistant/tolerant traits. The proportion of desired individuals for multiple characters in a population is obtained by multiplying together the proportion of desired individuals expected in the population for each character to be improved. This assumes that the characters are inherited independently, i.e., are not genetically linked.

These principles can be applied not only to traditionally bred lines, but to transgenic lines as well. Whether combining desirable traditional and transgenic traits via hybridization of transgenic lines or co-transformation of multiple genes into one line, the combined effect on yield are likely to be multiplicative. For example, if the probability that suitable yields and disease resistance are found in 1% of lines transformed with a single herbicide resistance gene, then the probability that combining three herbicide resistance genes in a line with suitable yield and disease resistance ought to be 0.01×0.01×0.01 or $1\times10^{-6}$.

The likelihood of identifying a line with a suitable combination of traits is further reduced when considering the potential effects of a transgene on the regulation of metabolism within a plant. For example, one can consider the potential effect of genes conferring resistance to glyphosate, glufosinate, and sulfonylureas or imidazolanones. The genes conferring these traits are, respectively, a gene encoding the enzyme 5-enolpyruvylshikimate-3-phosphate synthase (EPSPS), a transgene encoding the enzyme phosphinothricin acetyl transferase (PAT), and a gene encoding a mutant acetolactate syntase (ALS) enzyme. The biochemical steps affected by these genes is illustrated in Scheme 1. In the case of PAT, the effect is not to catalyze the reaction shown, but to counteract the effect of phosphinothricin, which inhibits the enzyme glutamine synthase. Two of the genes (EPSPS and ALS) affect closely related biochemical reactions in the synthesis of amino acids.

In commercial versions of plants which are resistant to glyphosate, a gene is introduced which is controlled by the cauliflower mosaic virus 35S RNA promoter. Because this promoter is constitutively expressed, the transgenic enzyme is not under the same controls as the endogenous EPSPS promoter. Consequently, the flow of carbon through the reaction catalyzed by EPSPS would not be subject to the regulatory mechanisms which would normally be present. Thus, the amount of PEP (which can be assumed, along with other substrates normally in the cell, to be at sub-saturating levels) going through the pathway to phenylalanine, tyrosine, and tryptophan would probably be greater than normal, and could result in a shortage of PEP necessary for the production of valine,

SCHEME 1

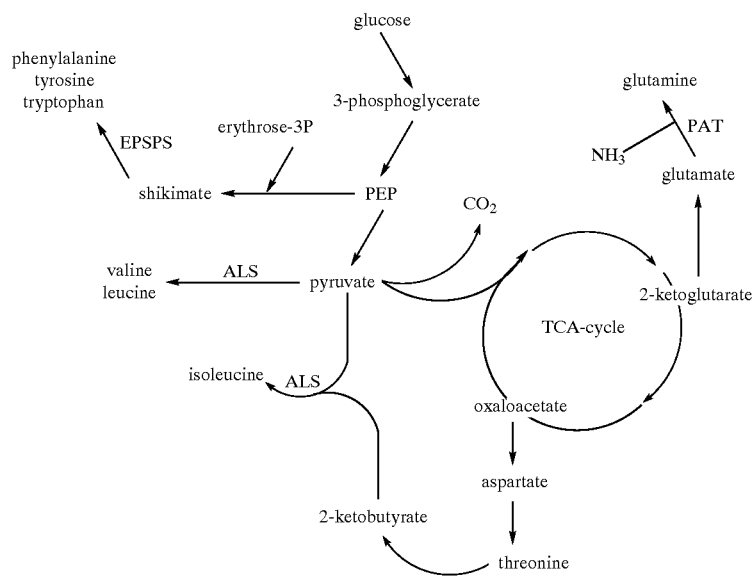

leucine, and isoleucine through the pathway involving ALS. This could be the reason for our observations that many lines transformed with EPSPS are not acceptable with respect to yield, and many must be screened for an acceptable line to be selected. Presumably these few acceptable lines have background genotypes which compensate for or are unaffected by the perturbations caused by the introduced gene.

Similar scenarios can be envisioned for the selection of ALS mutants resistant to sulfonylureas and transgenic lines tolerant to Liberty™ herbicide. In the case of lines containing the ALS mutants, characteristics of the mutant enzyme (either $K_m$ and/or $V_{max}$) may have been affected. In the case of lines containing the introduced PAT gene, energy resources must be diverted to produce the new enzyme at levels suitable to confer herbicide tolerance.

When these lines are combined by breeding, the background genotypes which have adjusted to the introduced or mutant genes are combined, and new genotypes must be selected. Likewise, when the genes are introduced by transformation together, the adjustments made by the background genotype must occur as well. Therefore, the frequency of genotypes with suitable yield will be reduced accordingly. Surprisingly, we have been able to select genotypes with unaffected yield resulting from the crossing of lines transformed with single genes.

Using similar techniques and other techniques well known in the art, resistance genes to other herbicides can also be combined. The instant invention relates to herbicide resistance genes, constructs, promoters and methods of incorporating the resistance genes into commercial inbreds, hybrids and varieties of many plant crops including but not limited to, the crops of corn, cotton, soybeans, canola, sunflowers, sorghum, wheat, barley, triticales, alfalfa, tomato, pepper, broccoli, rose, impatiens, carnation, geranium and petunia. Suitable genes, promoters and methods may be found in *Herbicide-Resistant Crops*, Editor Stephen O. Duke, CRC Lewis Publishers, 1996; *Herbicide Resistance in Plants*, Editors Stephen B. Powles and Joseph A. M. Holtum, CRC Press Inc., 1994; and in U.S. Pat. No. 5,084, 082; 5,359,142; 5,322,938; 5,424,200; 5,164,316; 5,352, 605; 5,094,945; 4,535,600 and 4,940,835, all of which are incorporated herein by reference. While it is very difficult to develop the first commercially acceptable inbred or variety having resistance to more than one herbicide, once an elite inbred or variety is produced then the combined herbicide resistance characteristic can be readily transferred to other inbreds, hybrids and varieties with appropriate backcross and selection to maintain the desirable traits.

As used herein, the term "plant" includes plant cells, plant protoplasts, plant cells of tissue culture from which soybean plants can be regenerated, plant calli, plant clumps, and plant cells that are intact plants or parts of plants such as pollen, flowers, seeds, leaves, stems and the like.

EXAMPLES

The following examples are provided to further illustrate the present invention and are not intended to limit the invention beyond the limitations set forth in the appended claims.

Example 1

Herbicide resistance genes are introduced individually or in combination into plant genomes by a variety of methods. One preferred means of gene introduction is the use of microprojectile bombardment. For example, a gene for herbicide tolerance, such as the CP4 EPSPS conferring tolerance to a level of resistance to glyphosate is placed under the control of a promoter such as the Cauliflower Mosaic Virus (CaMV) 35S promoter. The promoter and a nontranslated leader sequence such as the alfalfa mosaic virus, tobacco mosaic virus, or cucumber mosaic virus leader, is fused to the 5' end of the gene. A promoter such as the CaMV 35S promoter has its activity enhanced by duplication of a portion of the promoter sequence. A transcription termination sequence such as the CaMV 35S terminator or the nopaline synthase (nos) terminator is fused to the gene at the 3' end. Methods for accomplishing these constructions are well known in the art. This construction is introduced into an *E. coli* plasmid for propagation and for transformation. This plasmid also contains a marker gene such as the gus marker—a gene well known in the art, encoding the enzyme β-glucuronidase, whose expression in plant tissues allows the in situ visual identification of cells which have received the transforming DNA.

DNA of the construct described above is introduced into plant genomes by precipitation onto microscopic gold or tungsten particles and acceleration of these particles into plant tissue by means of a device such as the DuPont PDS 1000, a commercially available device for conducting plant transformations by means of microprojectile bombardment. Methods for accomplishing this are well known in the art. Plant tissue such as embryogenic callus or shoot meristems are chosen as the target for bombardment. These tissues are arranged in a petri dish in such a way as to offer the best possibility of successful transformation. Parameters are well-known in the art, but modifications and adjustments must be made in these parameters to optimize the transformation of each species. The particles coated with DNA are spread on a disc of mylar, which is loaded into the microprojectile apparatus. The mylar disc is accelerated until its flight is impeded by a stopping screen. The disc is stopped, but the particles continue their progress through the apparatus until they become embedded in the target plant tissue.

Selection of transformed tissue and then regeneration of these tissues into whole plants are accomplished by various methods. Some use the gene conferring herbicide tolerance to select plant cells which have incorporated the DNA, others make use of the accompanying gus gene as an indicator of transformation events, and then physically selecting or isolating transformed tissue. Such methods are well described in the literature. Methods for regenerating transformed tissue into whole plants are well-known in the art; especially known are the parameters which must be adjusted for each species or genotype in order to achieve efficient rates of regeneration.

Genes conferring a level of resistance to glyphosate and gluphosinate are introduced in combination by constructing them separately, mixing the constructs, and then precipitating them together onto the same gold or tungsten particles. This method depends upon the ability to select for cells which have received all of the genes of interest. Double selection is applied, exposing the cells to both herbicides simultaneously or in sequence, thus allowing the survival only of those cells which have incorporated both herbicide tolerance genes. Assaying for gus gene activity is also used in combination, if only one of the constructs is made in tandem with the gus gene. In situ assays are made of tissues which are expressing gus, and those tissues are then physically isolated. Selection is then imposed on those tissues by application of the herbicide for which resistance is encoded by the gene which was not constructed in tandem with gus. The order is also reversed, i.e. selection may be imposed first, followed by gus assays.

Alternatively, the genes are introduced together by introducing them into the same *E. coli* plasmid, with or without a gus marker gene. Each gene is under the control of its own promoter, untranslated leader (if appropriate), and 3' terminator region as described above, and inserted into appropriate cloning sites in the transformation vector. After microprojectile bombardment, selection of transformed tissue and subsequent regeneration into plants is then accomplished by physical selection of transformed tissue identified in situ via gus assays. In addition, selection is imposed by exposure of the cells to one or both herbicides, either simultaneously or sequentially.

The above illustration of the means by which genes can be combined in transformations describe methods well known in the art. They are provided as examples only, and are not meant to be an exhaustive description of the various means by which genes can be introduced into plant genomes. Other methods, such as electroporation, Agrobacterium-mediated transformation, or other methods may be used to obtain the desired results.

Example 2
Development of Soybean Variety 924181339 Having a Level of Resistance to Both Glyphosate and Sulfonylurea Herbicides 924181339 has resistance to Roundup™ herbicide and also contains the ALS inhibitorgene for sulfonylurea resistance. 924181339 is a mid maturity group IV variety with moderate resistance to Soybean Cyst Nematode, race 3 and race 14. 924181339 is well adapted to Maryland, Kentucky and Illinois and does well on heavier soil types. The present invention has improved plant type, with good lodging resistance and good tolerance to Pod and Stem Blight (*Diaporthe phaseolorum*). A patent has been issued having U.S. Pat. No. 5,710,368 and is incorporated herein by reference.

In the Tables 1 and 2 that follow, the traits and characteristics of soybean cultivar 924181339 are compared to several competing varieties of commercial soybeans of similar maturity. In these tables, column 1 shows the Competitor Variety. Column 2 and 3 indicate the number of tests and years of testing. Column 4, 5 and 6 indicate the yield in bushels/acre for the instant invention, the Competitor Variety identified in column 1 and the difference, respectively. Column 7 and 8 indicate the days to maturity for the instant invention and Competitor Variety, respectively. Column 9 and 10 show plant height of the instant invention and Competitor Variety and column 11 and 12 show the lodging score for the instant invention and the Competitor Variety respectively. Lodging scores are rated 1=Best and 5=Worst.

TABLE 1

ASGROW RESEARCH YIELD TRIAL — HEAD TO HEAD COMPARISON
ASGROW 924181339 VS. COMPETITOR VARIETIES
LOCATIONS: ALL
'1339 IN THE TABLE REFERS TO ASGROW 924181339

| Competitor Variety | Number | | Yield, Bushel/Acre | | | Maturity | | Height | | Lodging | |
|---|---|---|---|---|---|---|---|---|---|---|---|
| (Other) | Tests | Years | '1339 | Other | Diff. | '1339 | Other | '1339 | Other | '1339 | Other |
| Asgrow A4922 | 16 | 1 | 55.5 | 55.5 | .0 | 24.9 | 27.8 | 41.1 | 40.6 | 2.3 | 2.4 |
| Asgrow A4715 | 16 | 1 | 55.5 | 53.3 | 2.2 | 24.9 | 26.6 | 41.1 | 39.1 | 2.3 | 1.9 |
| Asgrow A4539 | 16 | 1 | 55.5 | 55.1 | .3 | 24.9 | 24.3 | 41.1 | 37.1 | 2.3 | 1.9 |
| Asgrow AG4401 | 16 | 1 | 55.5 | 53.0 | 2.5 | 24.9 | 25.2 | 41.1 | 40.9 | 2.3 | 2.1 |
| Pioneer 9472 | 16 | 1 | 55.5 | 55.4 | .1 | 24.9 | 24.3 | 41.1 | 40.2 | 2.3 | 2.7 |
| HS 4824 | 16 | 1 | 55.5 | 58.5 | -3.0 | 24.9 | 28.9 | 41.1 | 41.2 | 2.3 | 2.6 |

TABLE 2

ASGROW RESEARCH YIELD TRIAL — HEAD TO HEAD COMPARISON
ASGROW 924181339 VS. COMPETITOR VARIETIES
LOCATIONS: ALL NORTHERN LOCATIONS
'1339 IN THE TABLE REFERS TO ASGROW 924181339

| Competitor Variety | Number | | Yield, Bushel/Acre | | | Maturity | | Height | | Lodging | |
|---|---|---|---|---|---|---|---|---|---|---|---|
| (Other) | Tests | Years | '1339 | Other | Diff. | '1339 | Other | '1339 | Other | '1339 | Other |
| Asgrow A4922 | 11 | 1 | 54.9 | 54.9 | .0 | 28.5 | 32.5 | 41.5 | 40.0 | 2.4 | 2.4 |
| Asgrow A4715 | 11 | 1 | 54.9 | 53.0 | 1.9 | 28.5 | 31.6 | 41.5 | 38.9 | 2.4 | 2.2 |
| Asgrow A4539 | 11 | 1 | 54.9 | 55.3 | -.4 | 28.5 | 28.8 | 41.5 | 36.5 | 2.4 | 2.0 |
| Asgrow AG4701 | 11 | 1 | 54.9 | 53.2 | 1.7 | 28.5 | 31.8 | 41.5 | 44.0 | 2.4 | 2.6 |
| Asgrow AG4401 | 11 | 1 | 54.9 | 53.1 | 1.8 | 28.5 | 29.5 | 41.5 | 40.8 | 2.4 | 2.2 |
| Pioneer 9472 | 11 | 1 | 54.9 | 56.0 | -1.1 | 28.5 | 27.7 | 41.5 | 40.8 | 2.4 | 2.8 |
| HS 4824 | 11 | 1 | 54.9 | 57.8 | -3.0 | 28.5 | 33.1 | 41.5 | 41.6 | 2.4 | 2.7 |

Soybean cultivar 924181339 was developed from the cross A4045× (A4138×40-3-2). $F_2$ and $F_3$ plants were advanced by a modified pedigree selection. In 1994, $F_3$ derived $F_4$ lines were selected and entered in a four location preliminary yield trial. In 1995 the line was advanced to a 16 location yield trial.

Example 3
Development of Soybean Variety 928933959 Having a Level of Resistance to Glyphosate and Sulfonylurea Herbicides Soybean cultivar 928933959 was developed from the cross A3304×A3510² (A3237×40-3-2). $F_2$ and $F_3$ plants were advanced by a modified pedigree selection. In 1994, $F_3$ derived $F_4$ lines were selected and entered in a two location preliminary yield trial. In 1995 the line was advanced to a 20 location yield trial.

928933959 is a late maturity group III variety with resistance to Sulfonylurea herbicides, Roundup Ready™ herbicide, as well as $Rps_1{}^c$, conferring resistance to many races of Phytophthora Root Rot. The present invention is an improved plant type, with excellent emergence and which is adapted to heavier soil types. 928933959 has good iron chlorosis tolerance and is adapted to double crop situations and to drilled, 15 inch or 30 inch rows. A patent has been issued having U.S. Pat. No. 5,659,120 and is incorporated herein by reference.

In Tables 3 and 4 that follow, the traits and characteristics of soybean cultivar 928933959 are compared to several competing varieties of commercial soybeans of similar maturity. In these tables, column 1 shows the Competitor Variety. Column 2 and 3 indicate the number of tests and years of testing. Column 4, 5 and 6 indicate the yield in bushels/acre for the instant invention, the Competitor Variety identified in column 1 and the difference, respectively. Column 7 and 8 indicate the days to maturity for the instant invention and Competitor Variety, respectively. Column 9 and 10 show plant height of the instant invention and Competitor Variety and column 11 and 12 show the lodging score for the instant invention and the Competitor Variety respectively. Lodging scores are rated 1=Best and 5=Worst.

Example 4
Development of Soybean Variety 92417111 Having a Level of Resistance to Glyphosate and Sulfonylurea Herbicides Soybean cultivar 92417111 was developed from the cross J88284 89Y142-36×R914210F3. $F_1$, $F_2$ and $F_3$ plants were advanced by a modified pedigree selection. $F_3$ derived $F_4$ lines were selected in 1994. In 1994 92417111 was entered in a yield trial at four locations where it ranked 14th of 50 entries. In 1995 92417111 was entered in a yield trial at 12 locations where it placed 17th of 38 entries. In 1996 92417111 was entered in a yield trial at 18 locations where it ranked 9th of 39 entries.

92417111 is a mid maturity group III variety with the Roundup Ready™ gene which makes the line tolerant of Roundup™ herbicide and also has a level of resistance to sulfonylurea herbicides. This line has good yield potential. 92417111 is a tall plant type which will make it well adapted to the heavier soils of the mid group III growing area, including Iowa, Illinois, Missouri, Indiana, Kansas, Nebraska and Ohio. A patent has been issued having U. S. Pat. No. 5,750,855 and is incorporated herein by reference.

In Tables 5 through 7 that follow, the traits and characteristics of soybean cultivar 92417111 are compared to several competing varieties of commercial soybeans of similar maturity. Each characteristic also indicates the number of locations which comprise the figures given. In these tables, column 1 shows the Competitor Variety. Column 2 and 3 indicate the number of tests and years of testing. Column 4, 5 and 6 indicate the yield in bushels/acre for the instant invention, the Competitor Variety identified in column 1 and the difference, respectively. Column 7 and 8 indicate the days to maturity for the instant invention and

TABLE 3

ASGROW RESEARCH YIELD TRIAL — HEAD TO HEAD COMPARISON
ASGROW 928933959 VS. COMPETITOR VARIETIES
'3959 SHOWN IN TABLE BELOW REFERS TO ASGROW 928933959
LOCATIONS: ALL

| Competitor Variety | Number | | Yield, Bushel/Acre | | | Maturity | | Height | | Lodging | |
|---|---|---|---|---|---|---|---|---|---|---|---|
| (Other) | Tests | Years | '3959 | Other | Diff. | '3959 | Other | '3959 | Other | '3959 | Other |
| Asgrow A3510 | 20 | 1 | 50.4 | 50.6 | -.2 | 39.1 | 41.4 | 39.3 | 35.6 | 2.0 | 1.5 |
| Asgrow A3431 | 20 | 1 | 50.4 | 53.0 | -2.6 | 39.1 | 37.8 | 39.3 | 36.1 | 2.0 | 1.3 |
| Asgrow A3313 | 20 | 1 | 50.4 | 49.2 | 1.3 | 39.1 | 38.6 | 39.3 | 33.1 | 2.0 | 1.3 |
| Asgrow A3732 | 20 | 1 | 50.4 | 50.6 | -.1 | 39.1 | 41.0 | 39.3 | 36.8 | 2.0 | 1.7 |
| Asgrow A3834 | 20 | 1 | 50.4 | 51.8 | -1.3 | 39.1 | 43.9 | 39.3 | 34.4 | 2.0 | 1.4 |
| Asgrow AG3501 | 20 | 1 | 50.4 | 43.3 | 7.2 | 39.1 | 41.9 | 39.3 | 36.5 | 2.0 | 1.5 |

TABLE 4

ASGROW RESEARCH YIELD TRIAL — HEAD TO HEAD COMPARISON
ASGROW 928933959 VS. COMPETITOR VARIETIES
'3959 SHOWN IN TABLE BELOW REFERS TO ASGROW 928933959
LOCATIONS: NORTH

| Competitor Variety | Number | | Yield, Bushel/Acre | | | Maturity | | Height | | Lodging | |
|---|---|---|---|---|---|---|---|---|---|---|---|
| (Other) | Tests | Years | '3959 | Other | Diff. | '3959 | Other | '3959 | Other | '3959 | Other |
| Asgrow A3510 | 12 | 1 | 47.3 | 46.1 | 1.2 | 24.0 | 26.0 | 37.9 | 34.9 | 1.9 | 1.5 |
| Asgrow A3431 | 12 | 1 | 47.3 | 50.1 | -2.9 | 24.0 | 23.5 | 37.9 | 35.5 | 1.9 | 1.3 |
| Asgrow A3313 | 12 | 1 | 47.3 | 45.4 | 1.9 | 24.0 | 23.7 | 37.9 | 32.3 | 1.9 | 1.3 |
| Asgrow A3732 | 12 | 1 | 47.3 | 45.7 | 1.6 | 24.0 | 26.3 | 37.9 | 35.5 | 1.9 | 1.5 |
| Asgrow A3834 | 12 | 1 | 47.3 | 45.8 | 1.4 | 24.0 | 28.5 | 37.9 | 32.8 | 1.9 | 1.3 |
| Asgrow AG3501 | 12 | 1 | 47.3 | 40.0 | 7.3 | 24.0 | 26.9 | 37.9 | 35.7 | 1.9 | 1.4 |

Competitor Variety, respectively. Column 9 and 10 show plant height in inches of the instant invention and Competitor Variety. Column 11 and 12 show the lodging score for the instant invention and the Competitor Variety respectively. Column 13 and 14 show the general rating scores for the instant invention and the Competitor Variety, respectively. Lodging and General Rating scores are rated 1=Best and 5=Worst.

TABLE 5A

HEAD TO HEAD COMPARISONS OF 92417111
LISTED BELOW AS '7111 — ALL YEARS — ALL LOCATIONS

| Other Variety or Hybrid | Loc. | Years | '7111 Yield Bu/A | Other Yield Bu/A | Diff | Loc. | '7111 Maturity >9/1 | Other Maturity >9/1 |
|---|---|---|---|---|---|---|---|---|
| Asgrow AG3601 | 32 | 2 | 55.9 | 54.5 | 1.4 | 9 | 25.3 | 27.6 |
| Asgrow A3834 | 32 | 2 | 55.9 | 57.1 | -1.2 | 9 | 25.3 | 29.3 |
| Asgrow A3510 | 32 | 2 | 55.9 | 54.0 | 1.9 | 9 | 25.3 | 25.0 |
| Asgrow A3732 | 32 | 2 | 55.9 | 55.7 | 0.2 | 9 | 25.3 | 27.9 |
| Asgrow AG3701 | 32 | 2 | 55.9 | 55.6 | 0.3 | 9 | 25.3 | 27.0 |
| Asgrow A3704 | 32 | 2 | 55.9 | 55.6 | 0.3 | 9 | 25.3 | 27.3 |
| Dekalb CX377 | 20 | 1 | 51.0 | 50.0 | 1.0 | | | |
| Dekalb CX394C | 20 | 1 | 51.0 | 46.9 | 4.1 | | | |
| Pioneer 9392 | 32 | 2 | 55.9 | 53.8 | 2.1 | 9 | 25.3 | 27.3 |
| Pioneer 9362 | 20 | 1 | 51.0 | 51.7 | -0.7 | | | |
| Growmark HS3948 | 12 | 1 | 64.2 | 64.0 | 0.2 | 9 | 25.3 | 30.4 |
| Growmark HS3551 | 12 | 1 | 64.2 | 62.9 | 1.2 | 9 | 25.3 | 27.3 |
| Growmark HSE392 | 12 | 1 | 64.2 | 66.1 | -1.9 | 9 | 25.3 | 29.6 |
| Stine 3260 | 20 | 1 | 51.0 | 51.9 | -0.9 | | | |
| Stine 3660 | 20 | 1 | 51.0 | 50.8 | 0.2 | | | |
| Asgrow A4138 | 12 | 1 | 64.2 | 64.7 | -0.5 | 9 | 25.3 | 30.0 |

TABLE 5B

CONTINUATION OF TABLE 5A

| Other Variety or Hybrid | Loc. | '7111 Plt Hgt inches | Other Plt Hgt inches | Loc. | '7111 Lodge (1–5) | Other Lodge (1–5) | Loc. | '7111 Gen Rtg (1–5) | Other Gen Rtg (1–5) |
|---|---|---|---|---|---|---|---|---|---|
| Asgrow AG3601 | 24 | 40.0 | 38.9 | 27 | 2.3 | 2.0 | 24 | 3.2 | 2.8 |
| Asgrow A3834 | 24 | 40.0 | 33.5 | 27 | 2.3 | 1.4 | 24 | 3.2 | 1.5 |
| Asgrow A3510 | 24 | 40.0 | 34.5 | 27 | 2.3 | 1.5 | 24 | 3.2 | 1.9 |
| A3732 | 24 | 40.0 | 36.3 | 27 | 2.3 | 1.7 | 24 | 3.2 | 2.3 |
| Asgrow AG3701 | 24 | 40.0 | 36.1 | 27 | 2.3 | 1.6 | 24 | 3.2 | 2.2 |
| Asgrow A3704 | 24 | 40.0 | 33.3 | 27 | 2.3 | 1.6 | 24 | 3.2 | 1.9 |
| Dekalb CX377 | 15 | 38.9 | 36.2 | 18 | 2.0 | 1.7 | 15 | 3.0 | 2.6 |
| Dekalb CX394C | 15 | 38.9 | 40.3 | 18 | 2.0 | 1.6 | 15 | 3.0 | 2.3 |
| Pioneer 9392 | 24 | 40.0 | 37.2 | 27 | 2.3 | 1.6 | 24 | 3.2 | 1.8 |
| Pioneer 9362 | 15 | 38.9 | 34.2 | 18 | 2.0 | 1.3 | 15 | 3.0 | 2.2 |
| Growmark HS3948 | 9 | 41.7 | 34.7 | 9 | 2.7 | 1.7 | 9 | 3.6 | 2.0 |
| Growmark HS3551 | 9 | 41.7 | 33.3 | 9 | 2.7 | 1.5 | 9 | 3.6 | 1.7 |
| Growmark HSE392 | 9 | 41.7 | 37.0 | 9 | 2.7 | 1.9 | 9 | 3.6 | 2.1 |
| Stine 3260 | 15 | 38.9 | 35.0 | 18 | 2.0 | 1.7 | 15 | 3.0 | 2.6 |
| Stine 3660 | 15 | 38.9 | 33.4 | 18 | 2.0 | 1.5 | 15 | 3.0 | 2.7 |
| Asgrow A4138 | 9 | 41.7 | 39.1 | 9 | 2.7 | 2.6 | 9 | 3.6 | 2.6 |

TABLE 6A

HEAD TO HEAD COMPARISONS OF 92417111
LISTED BELOW AS '7111 — ALL YEARS — EASTERN LOCATIONS

| Other Variety or Hybrid | Loc. | Years | '7111 Yield Bu/A | Other Yield Bu/A | Diff | Loc. | '7111 Maturity >9/1 | Other Maturity >9/1 |
|---|---|---|---|---|---|---|---|---|
| Asgrow AG3601 | 17 | 2 | 57.0 | 56.2 | 0.7 | 6 | 25.6 | 27.5 |
| Asgrow A3834 | 17 | 2 | 57.0 | 60.8 | -3.8 | 6 | 25.6 | 29.6 |
| Asgrow A3510 | 17 | 2 | 57.0 | 56.4 | 0.5 | 6 | 25.6 | 25.2 |
| Asgrow A3732 | 17 | 2 | 57.0 | 56.5 | 0.4 | 6 | 25.6 | 27.8 |
| Asgrow AG3701 | 17 | 2 | 57.0 | 56.9 | 0.1 | 6 | 25.6 | 26.9 |

TABLE 6A-continued

HEAD TO HEAD COMPARISONS OF 92417111
LISTED BELOW AS '7111 — ALL YEARS — EASTERN LOCATIONS

| Other Variety or Hybrid | Loc. | Years | '7111 Yield Bu/A | Other Yield Bu/A | Diff | Loc. | '7111 Maturity >9/1 | Other Maturity >9/1 |
|---|---|---|---|---|---|---|---|---|
| Asgrow A3704 | 17 | 2 | 57.0 | 57.3 | −0.3 | 6 | 25.6 | 27.2 |
| Dekalb CX377 | 11 | 1 | 53.3 | 53.8 | −0.5 | | | |
| Dekalb CX394C | 11 | 1 | 53.3 | 49.4 | 3.9 | | | |
| Pioneer 9392 | 17 | 2 | 57.0 | 55.7 | 1.2 | 6 | 25.6 | 27.5 |
| Pioneer 9362 | 11 | 1 | 53.3 | 53.9 | −0.6 | | | |
| ZZ Stat Mean | 17 | 2 | 57.0 | 55.7 | 1.2 | 6 | 25.6 | 27.4 |
| Growmark HS3948 | 6 | 1 | 63.7 | 64.9 | −1.2 | 6 | 25.6 | 30.4 |
| Growmark HS3551 | 6 | 1 | 63.7 | 62.9 | 0.8 | 6 | 25.6 | 27.1 |
| Growmark HSE392 | 6 | 1 | 63.7 | 66.8 | −3.1 | 6 | 25.6 | 29.7 |
| Stine 3260 | 11 | 1 | 53.3 | 55.4 | −2.1 | | | |
| Stine 3660 | 11 | 1 | 53.3 | 53.0 | 0.2 | | | |
| Asgrow A4138 | 6 | 1 | 63.7 | 64.2 | −0.5 | 6 | 25.6 | 29.9 |

TABLE 6B

CONTINUATION OF TABLE 6A

| Other Variety or Hybrid | Loc. | '7111 Plt Hgt inches | Other Plt Hgt inches | Loc. | '7111 Lodge (1–5) | Other Lodge (1–5) | Loc. | '7111 Gen Rtg (1–5) | Other Gen Rtg (1–5) |
|---|---|---|---|---|---|---|---|---|---|
| Asgrow AG3601 | 15 | 39.6 | 38.9 | 17 | 2.4 | 2.3 | 14 | 3.1 | 2.8 |
| Asgrow A3834 | 15 | 39.6 | 33.6 | 17 | 2.4 | 1.5 | 14 | 3.1 | 1.5 |
| Asgrow A3510 | 15 | 39.6 | 34.1 | 17 | 2.4 | 1.7 | 14 | 3.1 | 2.0 |
| A3732 | 15 | 39.6 | 36.0 | 17 | 2.4 | 1.9 | 14 | 3.1 | 2.4 |
| Asgrow AG3701 | 15 | 39.6 | 36.4 | 17 | 2.4 | 1.7 | 14 | 3.1 | 2.3 |
| Asgrow A3704 | 15 | 39.6 | 33.1 | 17 | 2.4 | 1.8 | 14 | 3.1 | 2.0 |
| Dekalb CX377 | 9 | 38.7 | 38.7 | 11 | 2.1 | 1.7 | 8 | 2.8 | 2.5 |
| Dekalb CX394C | 9 | 38.7 | 40.5 | 11 | 2.1 | 1.8 | 8 | 2.8 | 2.5 |
| Pioneer 9392 | 15 | 39.6 | 37.1 | 17 | 2.4 | 1.7 | 14 | 3.1 | 2.0 |
| Pioneer 9362 | 9 | 38.7 | 34.0 | 11 | 2.1 | 1.5 | 8 | 2.8 | 2.3 |
| ZZ Stat Mean | 15 | 39.6 | 36.4 | 17 | 2.4 | 1.8 | 14 | 3.1 | 2.3 |
| Growmark HS3948 | 6 | 40.9 | 33.5 | 6 | 2.8 | 1.8 | 6 | 3.5 | 2.1 |
| Growmark HS3551 | 6 | 40.9 | 32.3 | 6 | 2.8 | 1.6 | 6 | 3.5 | 1.8 |
| Growmark HSE392 | 6 | 40.9 | 35.3 | 6 | 2.8 | 2.1 | 6 | 3.5 | 2.3 |
| Stine 3260 | 9 | 38.7 | 35.1 | 11 | 2.1 | 2.0 | 8 | 2.8 | 2.7 |
| Stine 3660 | 9 | 38.7 | 33.8 | 11 | 2.1 | 1.8 | 8 | 2.8 | 2.8 |
| Asgrow A4138 | 6 | 40.9 | 37.8 | 6 | 2.8 | 2.7 | 6 | 3.5 | 2.7 |

TABLE 7A

HEAD TO HEAD COMPARISONS OF 92417111
LISTED BELOW AS '7111 — ALL YEARS — ALL LOCATIONS

| Other Variety or Hybrid | Loc. | Years | '7111 Yield Bu/A | Other Yield Bu/A | Diff | Loc. | '7111 Maturity >9/1 | Other Maturity >9/1 |
|---|---|---|---|---|---|---|---|---|
| Asgrow AG3601 | 15 | 2 | 54.8 | 52.5 | 2.3 | 3 | 24.7 | 27.6 |
| Asgrow A3834 | 15 | 2 | 54.8 | 52.9 | 1.8 | 3 | 24.7 | 28.8 |
| Asgrow A3510 | 15 | 2 | 54.8 | 51.2 | 3.5 | 3 | 24.7 | 24.7 |
| Asgrow A3732 | 15 | 2 | 54.8 | 54.8 | 0.0 | 3 | 24.7 | 28.1 |
| Asgrow AG3701 | 15 | 2 | 54.8 | 54.3 | 0.5 | 3 | 24.7 | 27.1 |
| Asgrow A3704 | 15 | 2 | 54.8 | 53.7 | 1.1 | 3 | 24.7 | 27.4 |
| Dekalb CX377 | 9 | 1 | 48.2 | 45.3 | 2.8 | | | |
| Dekalb CX394C | 9 | 1 | 48.2 | 43.8 | 4.4 | | | |
| Pioneer 9392 | 15 | 2 | 54.8 | 51.7 | 3.1 | 3 | 24.7 | 26.9 |
| Pioneer 9362 | 9 | 1 | 48.2 | 49.0 | −0.8 | | | |
| Growmark HS3948 | 6 | 1 | 64.7 | 63.1 | 1.6 | 3 | 24.7 | 30.3 |
| Growmark HS3551 | 6 | 1 | 64.7 | 63.0 | 1.6 | 3 | 24.7 | 27.7 |
| Growmark HSE392 | 6 | 1 | 64.7 | 65.4 | −0.7 | 3 | 24.7 | 29.2 |
| Stine 3260 | 9 | 1 | 48.2 | 47.7 | 0.5 | | | |
| Stine 3660 | 9 | 1 | 48.2 | 48.1 | 0.1 | | | |
| Asgrow A4138 | 6 | 1 | 64.7 | 65.2 | −0.5 | 3 | 24.7 | 30.3 |

TABLE 7B

CONTINUATION OF TABLE 7A

| Other Variety or Hybrid | Loc. | '7111 Plt Hgt inches | Other Plt Hgt inches | Loc. | '7111 Lodge (1–5) | Other Lodge (1–5) | Loc. | '7111 Gen Rtg (1–5) | Other Gen Rtg (1–5) |
|---|---|---|---|---|---|---|---|---|---|
| Asgrow AG3601 | 9 | 40.7 | 38.9 | 10 | 2.1 | 1.6 | 10 | 3.4 | 2.8 |
| Asgrow A3834 | 9 | 40.7 | 33.3 | 10 | 2.1 | 1.1 | 10 | 3.4 | 1.4 |
| Asgrow A3510 | 9 | 40.7 | 35.0 | 10 | 2.1 | 1.2 | 10 | 3.4 | 1.9 |
| A3732 | 9 | 40.7 | 36.9 | 10 | 2.1 | 1.4 | 10 | 3.4 | 2.2 |
| Asgrow AG3701 | 9 | 40.7 | 35.8 | 10 | 2.1 | 1.4 | 10 | 3.4 | 2.1 |
| Asgrow A3704 | 9 | 40.7 | 33.5 | 10 | 2.1 | 1.3 | 10 | 3.4 | 1.9 |
| Dekalb CX377 | 6 | 39.3 | 37.5 | 7 | 1.9 | 1.6 | 7 | 3.3 | 2.6 |
| Dekalb CX394C | 6 | 39.3 | 40.1 | 7 | 1.9 | 1.4 | 7 | 3.3 | 2.0 |
| Pioneer 9392 | 9 | 40.7 | 37.2 | 10 | 2.1 | 1.3 | 10 | 3.4 | 1.4 |
| Pioneer 9362 | 6 | 39.3 | 34.5 | 7 | 1.9 | 1.1 | 7 | 3.3 | 2.0 |
| Growmark HS3948 | 3 | 43.3 | 37.1 | 3 | 2.5 | 1.4 | 3 | 3.7 | 1.8 |
| Growmark HS3551 | 3 | 43.3 | 35.2 | 3 | 2.5 | 1.3 | 3 | 3.7 | 1.4 |
| Growmark HSE392 | 3 | 43.3 | 40.2 | 3 | 2.5 | 1.6 | 3 | 3.7 | 1.7 |
| Stine 3260 | 6 | 39.3 | 34.7 | 7 | 1.9 | 1.3 | 7 | 3.3 | 2.5 |
| Stine 3660 | 6 | 39.3 | 32.9 | 7 | 1.9 | 1.1 | 7 | 3.3 | 2.7 |
| Asgrow A4138 | 3 | 43.3 | 41.7 | 3 | 2.5 | 2.3 | 3 | 3.7 | 2.4 |

Example 5

Development of Soybean Variety 93233925295 Having a Level of Resistance to Glyphosate and Sulfonylurea Herbicide Soybean cultivar 93233925295 was developed from the cross J88284 89Y142-36-16×YP93–1286. $F_1$, $F_2$ and $F_3$ plants were advanced by a modified pedigree selection. $F_3$ derived $F_4$ lines were selected in 1994. In 1995 93233925295 was entered in a yield trial at 12 locations where it ranked 6th of 38 entries. In 1996 93233925295 was entered in a yield trial at 14 locations.

93233925295 is an early maturity group IV variety with Phytophthora Root Rot resistance, conferred by the Rps1k gene. It also contains the Roundup Ready™ gene which makes this line tolerant of Roundup™ herbicide and also has a level of resistance to sulfonylurea herbicides. This line has good yield potential and appearance. 93233925295 is adapted to both clay and loam soils in the early group IV production areas of Kansas, Missouri, Illinois and Indiana. A patent application on 93233925295 was filed on Feb. 21, 1997 having Ser. No. 08/803,875 and is incorporated herein by reference.

In Tables 8 through 10 that follow, the traits and characteristics of soybean cultivar 93233925295 are compared to several competing varieties of commercial soybeans of similar maturity. Each characteristic also indicates the number of locations which comprise the figures given. In these tables, column 1 shows the Competitor Variety. Column 2 and 3 indicate the number of tests and years of testing. Column 4, 5 and 6 indicate the yield in bushels/acre for the instant invention, the Competitor Variety identified in column 1 and the difference, respectively. Column 7 and 8 indicate the days to maturity for the instant invention and Competitor Variety, respectively. Column 9 and 10 show plant height in inches of the instant invention and Competitor Variety. Column 11 and 12 show the lodging score for the instant invention and the Competitor Variety respectively. Column 13 and 14 show the general rating scores for the instant invention and the Competitor Variety, respectively. Lodging and General Rating scores are rated 1 =Best and 5=Worst.

TABLE 8A

HEAD TO HEAD COMPARISONS OF 93233925295
LISTED BELOW AS '5295 — ALL YEARS — ALL LOCATIONS

| Other Variety or Hybrid | Loc. | Years | '5295 Yield Bu/A | Other Yield Bu/A | Diff | Loc. | '5295 Maturity >9/1 | Other Maturity >9/1 |
|---|---|---|---|---|---|---|---|---|
| Asgrow A4138 | 13 | 1 | 64.6 | 67.7 | -3.1 | 10 | 28.8 | 27.5 |
| Asgrow A3834 | 25 | 2 | 59.2 | 62.0 | -2.9 | 10 | 28.8 | 27.8 |
| Asgrow A4045 | 12 | 1 | 53.3 | 52.3 | 1.0 | | | |
| Asgrow A4341 | 13 | 1 | 64.6 | 65.9 | -1.2 | 10 | 28.8 | 29.1 |
| Asgrow AG4401 | 13 | 1 | 64.6 | 63.1 | 1.5 | 10 | 28.8 | 30.9 |
| Dekalb CX445 | 13 | 1 | 64.6 | 63.4 | 1.2 | 10 | 28.8 | 28.9 |
| Dekalb CX434 | 13 | 1 | 64.6 | 63.8 | 0.8 | 10 | 28.8 | 29.2 |
| Pioneer 9444 | 13 | 1 | 64.6 | 64.2 | 0.4 | 10 | 28.8 | 27.4 |

TABLE 8B

CONTINUATION OF TABLE 8A

| Other Variety or Hybrid | Loc. | '5295 Plt Hgt inches | Other Plt Hgt inches | Loc. | '5295 Lodge (1–5) | Other Lodge (1–5) | Loc. | '5295 Gen Rtg (1–5) | Other Gen Rtg (1–5) |
|---|---|---|---|---|---|---|---|---|---|
| Asgrow A4138 | 9 | 36.2 | 38.5 | 10 | 2.0 | 2.7 | 10 | 1.9 | 2.9 |
| Asgrow A3834 | 20 | 38.2 | 32.7 | 22 | 1.9 | 1.4 | 22 | 2.0 | 1.5 |
| Asgrow A4045 | 11 | 39.9 | 37.8 | 12 | 1.8 | 2.0 | 12 | 2.0 | 2.5 |
| Asgrow A4341 | 9 | 36.2 | 33.9 | 10 | 2.0 | 1.8 | 10 | 1.9 | 2.1 |
| Asgrow AG4401 | 9 | 36.2 | 40.2 | 10 | 2.0 | 2.4 | 10 | 1.0 | 2.2 |
| Dekalb CX445 | 9 | 36.2 | 37.7 | 10 | 2.0 | 2.2 | 10 | 1.9 | 2.8 |
| Dekalb CX434 | 9 | 36.2 | 37.1 | 10 | 2.0 | 2.3 | 10 | 1.9 | 2.9 |
| Pioneer 9444 | 9 | 36.2 | 35.7 | 10 | 2.0 | 2.0 | 10 | 1.9 | 1.8 |

TABLE 9A

HEAD TO HEAD COMPARISONS OF 93233925295
LISTED BELOW AS '5295 — ALL YEARS — EASTERN LOCATIONS

| Other Variety or Hybrid | Loc. | Years | '5295 Yield Bu/A | Other Yield Bu/A | Diff | Loc. | '5295 Maturity >9/1 | Other Maturity >9/1 |
|---|---|---|---|---|---|---|---|---|
| Asgrow A4138 | 6 | 1 | 70.6 | 68.3 | 2.3 | 6 | 26.6 | 25.1 |
| Asgrow A3834 | 14 | 2 | 61.8 | 63.9 | -3.0 | 6 | 26.6 | 25.8 |
| Asgrow A4045 | 8 | 1 | 53.8 | 52.4 | 1.4 | | | |
| Asgrow A4341 | 6 | 1 | 70.6 | 72.4 | -1.8 | 6 | 26.6 | 27.3 |
| Asgrow AG4401 | 6 | 1 | 70.6 | 66.3 | 4.3 | 6 | 26.6 | 29.0 |
| Dekalb CX445 | 6 | 1 | 70.6 | 67.3 | 3.2 | 6 | 26.6 | 27.1 |
| Dekalb CX434 | 6 | 1 | 70.6 | 68.3 | 2.3 | 6 | 26.6 | 27.2 |
| Pioneer 9444 | 6 | 1 | 70.6 | 66.6 | 3.9 | 6 | 26.6 | 25.3 |

TABLE 9B

CONTINUATION OF TABLE 9A

| Other Variety or Hybrid | Loc. | '5295 Plt Hgt inches | Other Plt Hgt inches | Loc. | '5295 Lodge (1–5) | Other Lodge (1–5) | Loc. | '5295 Gen Rtg (1–5) | Other Gen Rtg (1–5) |
|---|---|---|---|---|---|---|---|---|---|
| Asgrow A4138 | 5 | 36.4 | 37.8 | 6 | 2.5 | 3.0 | 6 | 2.3 | 3.2 |
| Asgrow A3834 | 13 | 38.1 | 32.8 | 14 | 2.1 | 1.7 | 14 | 2.2 | 1.7 |
| Asgrow A4045 | 8 | 39.1 | 37.0 | 8 | 1.8 | 2.1 | 8 | 2.1 | 2.6 |
| Asgrow A4341 | 5 | 36.4 | 33.7 | 6 | 2.5 | 2.0 | 6 | 2.3 | 1.9 |
| Asgrow AG4401 | 5 | 36.4 | 39.6 | 6 | 2.5 | 2.8 | 6 | 2.3 | 2.5 |
| Dekalb CX445 | 5 | 36.4 | 37.7 | 6 | 2.5 | 2.6 | 6 | 2.3 | 2.8 |
| Dekalb CX434 | 5 | 36.4 | 37.2 | 6 | 2.5 | 2.7 | 6 | 2.3 | 3.0 |
| Pioneer 9444 | 5 | 36.4 | 34.9 | 6 | 2.5 | 2.4 | 6 | 2.3 | 2.2 |

TABLE 10A

HEAD TO HEAD COMPARISONS OF 93233925295
LISTED BELOW AS '5295 — ALL YEARS — WESTERN LOCATIONS

| Other Variety or Hybrid | Loc. | Years | '5295 Yield Bu/A | Other Yield Bu/A | Diff | Loc. | '5295 Maturity >9/1 | Other Maturity >9/1 |
|---|---|---|---|---|---|---|---|---|
| Asgrow A4138 | 7 | 1 | 59.6 | 67.2 | -7.6 | 4 | 32.0 | 31.2 |
| Asgrow A3834 | 11 | 2 | 56.9 | 59.7 | -2.7 | 4 | 32.0 | 30.7 |
| Asgrow A4045 | 4 | 1 | 52.3 | 52.2 | 0.1 | | | |
| Asgrow A4341 | 7 | 1 | 59.6 | 60.3 | -0.8 | 4 | 32.0 | 31.7 |

TABLE 10A-continued

HEAD TO HEAD COMPARISONS OF 93233925295
LISTED BELOW AS '5295 — ALL YEARS — WESTERN LOCATIONS

| Other Variety or Hybrid | Loc. | Years | '5295 Yield Bu/A | Other Yield Bu/A | Diff | Loc. | '5295 Maturity >9/1 | Other Maturity >9/1 |
|---|---|---|---|---|---|---|---|---|
| Asgrow AG4401 | 7 | 1 | 59.6 | 60.4 | −0.9 | 4 | 32.0 | 33.6 |
| Dekalb CX445 | 7 | 1 | 59.6 | 60.1 | −0.5 | 4 | 32.0 | 31.7 |
| Dekalb CX434 | 7 | 1 | 59.6 | 60.0 | −0.4 | 4 | 32.0 | 32.2 |
| Pioneer 9444 | 7 | 1 | 59.6 | 62.2 | −2.6 | 4 | 32.0 | 30.5 |

TABLE 10B

CONTINUATION OF TABLE 10A

| Other Variety or Hybrid | Loc. | '5295 Plt Hgt inches | Other Plt Hgt inches | Loc. | '5295 Lodge (1–5) | Other Lodge (1–5) | Loc. | '5295 Gen Rtg (1–5) | Other Gen Rtg (1–5) |
|---|---|---|---|---|---|---|---|---|---|
| Asgrow A4138 | 4 | 35.9 | 39.4 | 4 | 1.3 | 2.2 | 4 | 1.4 | 2.4 |
| Asgrow A3834 | 7 | 38.5 | 32.5 | 8 | 1.5 | 1.1 | 8 | 1.6 | 1.2 |
| Asgrow A4045 | 3 | 41.8 | 40.0 | 4 | 1.6 | 1.8 | 4 | 1.9 | 2.1 |
| Asgrow A4341 | 4 | 35.9 | 34.0 | 4 | 1.3 | 1.3 | 4 | 1.4 | 2.4 |
| Asgrow AG4401 | 4 | 35.9 | 40.9 | 4 | 1.3 | 1.9 | 4 | 1.4 | 1.9 |
| Dekalb CX445 | 4 | 35.9 | 37.7 | 4 | 1.3 | 1.5 | 4 | 1.4 | 2.8 |
| Dekalb CX434 | 4 | 35.9 | 37.0 | 4 | 1.3 | 1.5 | 4 | 1.4 | 2.9 |
| Pioneer 9444 | 4 | 35.9 | 36.7 | 4 | 1.3 | 1.4 | 4 | 1.4 | 1.3 |

Example 6

Development of Soybean Variety 89248009206 Having Resistance to Sulfonylurea and Glufosinate Herbicide Soybean cultivar 89248009206 was developed from the cross (A2872×A2967)×[A5403×(Chamberlain×W20)]. Single plants from the F$_4$ bulk population were individually selected. In 1991, these lines were tested in experimental plots in 6 locations in the midwest. The highest yielding lines were retained for additional testing at 24 locations in 1992. Additional testing was conducted during 1993 at 22 locations where the lines were adapted and in 1994 at 71 locations. 89248009206 was transformed by introducing plasmid DNA through particle acceleration into Asgrow A2704. The plasmid contained synthetic versions of the pat gene derived from *Streptomyces viridochromogenes* which confers resistance to glufosinate herbicide (Liberty™). 89248009206 also has a level of resistance to sulfonylurea herbicides. A patent has been issued having U.S. Pat. No. 6,177,617 and is incorporated herein by reference.

In Table 11 that follows, the traits and characteristics of soybean cultivar 89248009206 as compared to the soybean cultivar A2704 variety are shown. In this table, column 1 shows the Variety. Column 2 indicates the Yield in bushels/acre for each cultivar. Column 3 indicates the approximate maturity date. Column 4 shows each individual plant's height in inches and column 5 indicates a lodging score for each cultivar. Lodging scores are rated 1=Best and 5=Worst. The bottom row of the table indicates the standard error for each trait.

In Table 12 that follows, column 1 shows the variety. Column 2 indicates the number of locations tested. Column 3 shows the percent of protein and column 4 indicates the percent of oil in the harvested seed.

In Table 13 that follows, the traits and characteristics of soybean cultivar A2704 are compared to several competing varieties of commercial soybeans of similar maturity. In this table, column 1 shows the Competitor Variety. Column 2 and 3 indicate the number of tests and years of testing. Column 4, 5 and 6 indicate the yield in bushels/acre for the instant invention, the Competitor Variety (in column 1) and the difference, respectively. Column 7 and 8 indicate the days of maturity for the instant invention and Competitor Variety, respectively. Column 9 and 10 show height of the instant invention and Competitor Variety and column 11 and 12 show the lodging score for the instant invention and the Competitor Variety respectively. Lodging scores are rated 1=Best and 5=Worst.

TABLE 11

AGRONOMIC DATA
MATURITY GROUP II
LIBERTY LINK ™ VARIETY 89248009206 AS COMPARED TO A2704

| VARIETY | YIELD (BU/A) | MATURITY | HEIGHT (INCHES) | LODGING |
|---|---|---|---|---|
| A2704 | 61.6 | September 28.5 | 35.50 | 1.40 |
| 89248009206 | 61.9 | September 30.5 | 31.80 | 1.70 |
| Standard Error | 1.2 | 0.28 | 0.62 | 0.26 |

TABLE 12

AGRONOMIC DATA
PROTEIN AND OIL DATA
LIBERTY LINK ™ VARIETY 89248009206 AS COMPARED TO A2704

| VARIETY | LOCATIONS | PROTEIN | OIL |
|---|---|---|---|
| A2704 | 6 | 40.7 | 19.7 |
| 89248009206 | 6 | 41.2 | 19.3 |

TABLE 13

ASGROW RESEARCH TRIAL — HEAD TO HEAD COMPARISON
ASGROW A2704 vs. LISTED COMPETITORS
91, 92, 93, 94
ALL LOCATIONS

| Competitor Variety | Number | | Yield, Bushel/Acre | | | Maturity | | Height | | Lodging | |
|---|---|---|---|---|---|---|---|---|---|---|---|
| (Other) | Tests | Years | A2704 | Other | Diff. | A2704 | Other | A2704 | Other | A2704 | Other |
| FP2833 | 47 | 2 | 62.8 | 64.6 | 1.8 | 21.9 | 21.9 | 35.6 | 32.2 | 2.0 | 1.3 |
| Asgrow XP2604 | 51 | 3 | 62.9 | 61.1 | 1.9 | 25.7 | 24.6 | 37.4 | 36.2 | 1.9 | 1.6 |
| Asgrow A2835 | 53 | 3 | 62.5 | 61.6 | .9 | 22.2 | 22.2 | 35.6 | 33.9 | 2.0 | 1.8 |
| Asgrow A2396 | 83 | 4 | 61.3 | 57.4 | 3.9 | 24.8 | 18.6 | 36.4 | 35.1 | 1.9 | 1.7 |
| Asgrow A2543 | 12 | 2 | 60.6 | 55.8 | 4.7 | 24.0 | 24.3 | 36.3 | 29.3 | 1.8 | 1.7 |
| Asgrow A2506 | 77 | 3 | 61.7 | 57.8 | 3.9 | 25.0 | 20.4 | 36.4 | 32.4 | 2.0 | 1.7 |
| Asgrow A2242 | 55 | 2 | 63.3 | 61.6 | 1.8 | 24.4 | 17.8 | 38.1 | 32.9 | 2.0 | 1.7 |
| Asgrow A2943 | 47 | 2 | 62.8 | 59.4 | 3.4 | 21.9 | 24.5 | 35.6 | 37.4 | 2.0 | 1.8 |
| Asgrow A2722 | 47 | 2 | 63.1 | 61.8 | 1.3 | 22.2 | 21.6 | 35.6 | 33.6 | 2.0 | 2.0 |
| Stine 2250 | 47 | 2 | 63.0 | 61.5 | 1.5 | 22.0 | 17.3 | 35.7 | 31.0 | 2.0 | 1.7 |
| Pioneer 9231 | 45 | 2 | 63.4 | 58.3 | 5.1 | 26.1 | 20.3 | 37.8 | 32.8 | 2.0 | 1.7 |
| Pioneer 9232 | 5 | 1 | 75.2 | 71.4 | 3.8 | 21.0 | 13.9 | 40.3 | 33.6 | 2.5 | 1.9 |
| Pioneer 9241 | 34 | 2 | 59.8 | 56.9 | 2.9 | 27.2 | 21.0 | 37.1 | 30.3 | 2.1 | 1.8 |
| Pioneer 9252 | 13 | 1 | 73.8 | 67.8 | 6.0 | 21.6 | 15.5 | 39.2 | 34.6 | 1.8 | 1.6 |
| Pioneer 9273 | 47 | 2 | 63.0 | 61.0 | 2.0 | 21.8 | 18.8 | 36.0 | 32.3 | 2.0 | 1.8 |
| Depf CX232 | 21 | 1 | 71.8 | 68.3 | 3.5 | 22.1 | 14.5 | 37.5 | 33.6 | 1.8 | 1.6 |
| Depf CX267 | 5 | 1 | 75.2 | 68.3 | 6.8 | 21.0 | 19.4 | 40.3 | 40.5 | 2.5 | 3.4 |
| Dair DSR250 | 5 | 1 | 75.2 | 72.4 | 2.8 | 21.0 | 20.7 | 40.3 | 35.4 | 2.5 | 1.9 |
| Laol 2494 | 21 | 1 | 71.8 | 70.5 | 1.3 | 22.1 | 16.4 | 37.5 | 33.9 | 1.8 | 1.6 |
| Laol 2838 | 5 | 1 | 75.2 | 74.2 | 1.0 | 21.0 | 18.4 | 40.3 | 38.7 | 2.5 | 2.7 |
| Stine 2490 | 5 | 1 | 75.2 | 72.8 | 2.4 | 21.0 | 24.4 | 40.3 | 37.6 | 2.5 | 2.3 |
| Noki S24-92 | 5 | 1 | 75.2 | 74.3 | .8 | 21.0 | 14.8 | 40.3 | 34.6 | 2.5 | 2.1 |
| Noki S25-07 | 5 | 1 | 75.2 | 65.2 | 9.9 | 21.0 | 18.0 | 40.3 | 42.1 | 2.5 | 3.3 |
| Noki S28-01 | 25 | 1 | 68.1 | 63.6 | 4.5 | 17.9 | 18.0 | 38.9 | 36.5 | 2.1 | 2.4 |

Example 7

Testing Procedures for Combined Glyphosate (RR) and Sulfonylurea (STS) Resistance Genotypes Studies were conducted in 1994 at three locations including Lexington, Ky.; Galena, Md.; and Queenstown, Md. to verify that the inclusion of the ALS resistance trait in soybean with the glyphosate resistance trait does not influence resistance to either Roundup and Synchrony. Glyphosate is the active ingredient in Roundup™ and chlorimuron and thifensulfuron are the active ingredients in Synchrony™. The entire plot area was treated with standard herbicides prior to or at planting followed by in-season cultivation and/or manual removal as necessary to eliminate weed competition. Maturity group V varieties included 40-3-2 Roundup™ Ready (RR), A5545 STS, and QG5444 RR/STS (combined herbicide resistance) and were planted in rows spaced 30 inches apart. Maturity group provides an indication of geographic adaptation. Variety 40-3-2 was treated with Roundup™ at 24 fl oz/A (glyphosate at 0.56 lb/A acid equivalent) and 48 fl oz/A at the V3 (third trifoliolate leaf fully expanded) stage. A5545 was treated with Synchrony™ 25DF at 0.85 oz/A (chlorimuron at 0.16 plus thifensulfuron at 0.05 oz/A) at the V3 stage. These same herbicides were applied to QG5444 as well as tank-mix combinations at V5 (fifth trifoliolate leaf fully expanded) and reciprocating sequential combinations at V3 and V5. Adjuvants (nonionic surfactant and ammonium sulfate or urea/ammonium nitrate solution) were used at recommended rates. A control having no in-season treatment was included for each variety. Two middle rows of each plot were harvested and yields were converted to percent of control. Treatments were replicated four times in a randomized complete block design. As stated previously, yield is the final culmination of many distinguishable agronomic traits including traits such as seed yield, disease resistance (e.g. soybean cyst nematode, Phytophthora resistance, brown stem rot), emergence vigor, vegetative vigor, standability, and threshability. Yield is ascertained by volume or weight per unit area.

Vegetative stages (V stages) are designated numerically as V1, V2, V3 through $V_{(N)}$ except the first two stages, which are designated as VE (emergence) and VC (cotyledon stage). The last V stage is designated as $V_{(N)}$, where (n) represents the number for the last node stage of the specific variety. The (n) will fluctuate with variety and environmental differences. The V stages (node stages) following VC are defined and numbered according to the uppermost fully developed leaf node. A fully developed leaf node is one that has a leaf above it with unrolled or unfolded leaflets. In other words, the leaflet edges are no longer touching. The V3 stage, for example, is defined when the leaflets on the 1st (unifoliolate) through the 4th node leaf are unrolled. Similarly, the VC stage occurs when the unifoliolate leaves have unrolled.

The unifoliolate leaf node is the first node or reference point from which to begin counting upward to identify upper leaf node numbers. This node is unique in that the unifoliolate (simple) leaves are produced from it on opposite sides of the stem and are borne on short petioles. All other true leaves formed by the plant are trifoliolate (compound) leaves borne on long petioles, and are produced singularly (from different nodes) and alternately (from side to side) on the stem.

This system accurately identifies the stages of a soybean plant. However, all plants in a given field will not be in the same stage at the same time. When staging a field of soybeans, each specific V stage is defined only when 50% or more of the plants in the field are in or beyond that stage.

Studies in 1995 included maturity group (MG) III varieties AGR36001 RR, A3304 STS, and AGR36508 RR/STS (Towanda, Ill.; Tuscola, Ill.; and Atlantic, Iowa.); MG IV varieties AGR46006 RR, A4045 STS, and AGR41502 RR/STS (Ridgway, Ill. and Lexington, Ky.); and MG V varieties AGR5601 RR, A5545 STS, and AGR5333 STS/RR (Galena, Md. and College Park, Md.). RR varieties were treated with Roundup at 32 fl oz/A at V3 stage. STS varieties were treated with Synchrony 42DF at 0.5 oz/A (equivalent to Synchrony 25DF at 0.85 oz/A) plus Assure II (recommended for grass control) at 8 fl oz/A (quizalofop at 0.06 lb/A) at V3 stage. These same herbicides were applied to RR/STS varieties as well as Synchrony 0.5 oz/A plus Roundup at 16 and 32 fl oz/A, and Synchrony/Roundup (16 fl oz/A) as reciprocating sequential combinations at V3N3+7days.

Only RR/STS varieties were included in 1996 studies (928933959 at Towanda, Ill.; Tuscola, Ill.; and Atlantic, Ill.; and 924181339 at Lexington, Ky. and Marion, Ariz.). Roundup Ultra (improved Roundup formulation) was substituted for Roundup and was applied only at 32 fl oz/A (glyphosate at 0.75 lb/A) alone or in combinations with Synchrony. Poast Plus at 24 fl oz/A (sethoxydim at 0.19 lb/A) was substituted for Assure II in 1996. Adjuvants included surfactant (Roundup only) and crop oil concentrate and ammonium sulfate or urea/ammonium nitrate solution for Synchrony at recommended rates. In both years, a control was included as an additional treatment for each variety. Two or four 30-in rows of 4 or 6-row plots were harvested and yields converted to percent of control. Treatments were replicated 3 or 4 times in a randomized complete block design.

Example 8
1994 Results

Responses of a Roundup Ready variety, a STS variety, and a RR/STS stacked trait variety within maturity group V to herbicide treatments in 1994 are summarized in Table 22. Results indicate that the Roundup Ready and STS varieties exhibited tolerance to Roundup and Synchrony, respectively. The stacked trait variety exhibited tolerance to Roundup equal to that exhibited by the Roundup Ready variety and exhibited tolerance to Synchrony equal to that exhibited by the STS variety. Furthermore, the stacked trait variety displayed tolerance to a tank-mix combination and sequential combinations of Synchrony plus Roundup indicating that neither herbicide predisposes the stacked trait variety to injury to the partner herbicide.

TABLE 14

| Variety | Herbicide | Application Timing | Yield* (% control) |
| --- | --- | --- | --- |
| 40-3-2-RR | Control | — | 100.0 |
| 40-3-2-RR | Roundup 24 fl oz | V3 | 102.7 |
| 40-3-2-RR | Roundup 48 fl oz | V3 | 99.1 |
| A5545-STS | Control | — | 100.0 |
| A5545-STS | Synchrony 25DF 0.85 oz | V3 | 98.7 |
| QG5444-RR/STS | Control | — | 100.0 |
| QG5444-RR/STS | Roundup 24 fl oz | V3 | 96.8 |
| QG5444-RR/STS | Roundup 48 fl oz | V3 | 97.5 |
| QG5444-RR/STS | Synchrony 25DF 0.85 oz | V3 | 101.8 |
| QG5444-RR/STS | Synchrony 0.85 + Roundup 24 | V3 | 98.7 |
| QG5444-RR/STS | Synchrony 0.85 / Roundup 24 | V3/V5 | 98.6 |
| QG5444-RR/STS | Roundup 24 / Synchrony 0.85 | V3/V5 | 99.8 |

*1994 means across three locations (Lexington, KY; Galena, MD; and Queenstown, MD)

Example 9
1995 Results

Responses of a Roundup Ready variety, a STS variety, and a stacked trait variety (RR/STS) within maturity groups III, IV, and V to herbicide treatments in 1995 are summarized in Tables 15, 16, and 17. The Roundup Ready and STS varieties within each maturity group exhibited tolerance to Roundup and Synchrony, respectively. The stacked trait RR/STS varieties also exhibited tolerance to these herbicides applied singly, in tank-mix combinations, and in sequential combinations. These results indicate that neither herbicide interacts with the partner herbicide to cause injury in stacked trait varieties across a range of maturity groups.

TABLE 15

| Variety | Herbicide | Application Timing | Yield* (% control) |
| --- | --- | --- | --- |
| AGR36001-RR | Control | — | 100.0 |
| AGR36001-RR | Roundup 24 fl oz | V3 | 101.1 |
| A3304-STS | Control | — | 100.0 |
| A3304-STS | Synchrony 42DF 0.5 oz + Assure 8 fl oz | V3 | 98.6 |
| 92417111 | Control | — | 100.0 |
| 92417111 | Roundup 32 fl oz | V3 | 105.2 |
| 92417111 | Synchrony 42DF 0.5 oz + Assure 8 fl oz | V3 | 105.1 |
| 92417111 | Synchrony 0.5 + Roundup 16 | V3 | 102.6 |
| 92417111 | Synchrony 0.5 + Roundup 32 | V3 | 100.5 |
| 92417111 | Synchrony 0.5 / Roundup 16 | V3/V3 + 7da | 101.0 |
| 92417111 | Roundup 16 / Synchrony 0.5 | V3/V3 + 7da | 100.5 |
| LSD (.10) | | | NS |
| C.V.(%) | | | 8.5 |

*1995 means across three locations (Towanda, IL; Tuscola, IL; and Atlantic, IA)

TABLE 16

| Variety | Herbicide | Application Timing | Yield* (% control) |
| --- | --- | --- | --- |
| AGR46006-RR | Control | — | 100.0 |
| AGR46006-RR | Roundup 24 fl oz | V3 | 101.1 |
| A4045-STS | Control | — | 100.0 |

TABLE 16-continued

| Variety | Herbicide | Application Timing | Yield* (% control) |
|---|---|---|---|
| A4045-STS | Synchrony 42DF 0.5 oz + Assure 8 fl oz | V3 | 103.5 |
| AGR41502-RR/STS | Control | — | 100.0 |
| AGR41502-RR/STS | Roundup 32 fl oz | V3 | 104.6 |
| AGR41502-RR/STS | Synchrony 42DF 0.5 oz + Assure 8 fl oz | V3 | 104.0 |
| AGR41502-RR/STS | Synchrony 0.5 + Roundup 16 | V3 | 110.5 |
| AGR41502-RR/STS | Synchrony 0.5 + Roundup 32 | V3 | 108.3 |
| AGR41502-RR/STS | Synchrony 0.5 / Roundup 16 | V3/V3 + 7da | 102.6 |
| AGR41502-RR/STS | Roundup 16 / Synchrony 0.5 | V3/V3 + 7da | 106.6 |
| LSD (.10) | | | 5.2 |
| C.V.(%) | | | 5.6 |

*1995 means across two locations (Ridgway, IL and Lexington, KY)

TABLE 17

| Variety | Herbicide | Application Timing | Yield* (% control) |
|---|---|---|---|
| AGR5601-RR | Control | — | 100.0 |
| AGR5601-RR | Roundup 24 fl oz | V3 | 101.1 |
| A5545-STS | Control | — | 100.0 |
| A5545-STS | Synchrony 42DF 0.5 oz + Assure 8 fl oz | V3 | 103.5 |
| AGR5333-RR/STS | Control | — | 100.0 |
| AGR5333-RR/STS | Roundup 32 fl oz | V3 | 104.6 |
| AGR5333-RR/STS | Synchrony 42DF 0.5 oz + Assure 8 fl oz | V3 | 104.0 |
| AGR5333-RR/STS | Synchrony 0.5 + Roundup 16 | V3 | 110.5 |
| AGR5333-RR/STS | Synchrony 0.5 + Roundup 32 | V3 | 108.3 |
| AGR5333-RR/STS | Synchrony 0.5 / Roundup 16 | V3/V3 + 7da | 102.6 |
| AGR5333-RR/STS | Roundup 16 / Synchrony 0.5 | V3/V3 + 7da | 106.6 |
| LSD (.10) | | | NS |
| C.V.(%) | | | 17.1 |

*1995 means across two locations (Galena, MD and College Park, MD)

Example 10

1996 Results

Tables 18 and 19 summarize the responses of two stacked trait varieties (maturity groups III and IV) to herbicide treatments in 1996. Both varieties exhibited tolerance to Roundup Ultra and Synchrony applied individually and in various combinations. This confirms the inclusion of both Roundup Ready and STS traits in soybean do not influence its tolerance to Roundup Ultra (or Roundup) and Synchrony herbicides.

TABLE 18

| Variety | Herbicide | Application Timing | Yield* (% control) |
|---|---|---|---|
| 928933959 | Control | — | 100.0 |
| 928933959 | Roundup Ultra 32 fl oz | V3 | 99.3 |
| 928933959 | Synchrony 42DF 0.5 oz + Poast Plus 24 floz | V3 | 101.2 |
| 928933959 | Synchrony 0.5 + Roundup Ultra 32 | V3 | 99.6 |
| 928933959 | Synchrony 0.5 /Roundup Ultra 32 | V3/V3 + 7da | 98.9 |
| 928933959 | Roundup Ultra 32/Synchrony 0.5 | V3/V3 + 7da | 99.9 |
| LSD (.10) | | | NS |
| C.V.(%) | | | 2.9 |

*1996 means across three locations (Towanda, IL; Tuscola, IL; and Atlantic, IA)

TABLE 19

| Variety | Herbicide | Application Timing | Yield* (% control) |
|---|---|---|---|
| 924181339 | Control | — | 100.0 |
| 924181339 | Roundup Ultra 32 fl oz | V3 | 95.6 |
| 924181339 | Synchrony 42DF 0.5 oz + Poast Plus 24 floz | V3 | 99.1 |

TABLE 19-continued

| Variety | Herbicide | Application Timing | Yield* (% control) |
|---|---|---|---|
| 924181339 | Synchrony 0.5 + Roundup Ultra 32 | V3 | 98.2 |
| 924181339 | Synchrony 0.5 /Roundup Ultra 32 | V3/V3 + 7da | 94.0 |
| 924181339 | Roundup Ultra 32/Synchrony 0.5 | V3/V3 + 7da | 98.5 |
| LSD (.10) | | | NS |
| C.V.(%) | | | 5.5 |

*1996 means across two locations (Lexington, KY and Marion, AR)

Example 11
LL/STS Testing Procedures

Research was conducted in 1996 at five locations (Oxford, Ind.; Tuscola, Ill.;Atlantic, Iowa.; Huxley, Iowa.; and Williams, Iowa.) to examine the effect of inclusion of the liberty-Link (LL) trait in soybean with the STS trait on tolerance to Liberty and Reliance or Synchrony. The entire plot area was treated with standard herbicides prior to or at planting followed by in-season cultivation and/or manual removal as necessary to eliminate weed competition. 89248009206 LL/STS (combined LL and STS traits) variety was planted in rows spaced 30 inches apart. Treatments at Huxley and Williams, Iowa. included Liberty alone at 28 fl oz (glufosinate at 0.36 lb) and 56 fl oz/A, Reliance 25DF at 0.5 (chlorimuron at 0.06 plus thifensulfuron at 0.06 oz/A) and 1.0 oz/A in combination with Poast Plus at 24 fl oz/A (sethoxydim at 0.19 lb/A), Reliance plus liberty at 0.5 oz plus 28 fl oz and 1.0 oz plus 56 fl oz/A as tank-mix treatments at the V3 (third trifoliolate leaf fully expanded) stage and reciprocating sequential treatments at V3/V3 plus 7 days, and Liberty at 105 fl oz/A at V3 plus 7 days. Synchrony 42DF (0.5 oz/A=chlorimuron at 0.16 plus thifensulfuron at 0.05 oz/A) was substituted for Reliance 25DF at the other locations. Ammonium sulfate for Liberty alone or crop oil concentrate and ammonium sulfate for treatments that included Reliance or Synchrony were used as a adjuvants at recommended rates. A control having no in-season treatment, was included as an additional treatment. Two middle rows or all four rows of each plot were harvested and yields were converted to percent of control. Treatments were replicated four or six times (Huxley and Oxford) in a randomized complete block design.

Example 12
1996 LL/STS Results

Response of the LL/STS stacked trait soybean to Liberty and Reliance herbicides in 1996 are summarized in Tables 20 and 21. Tolerance was exhibited to these herbicides at 1×(Liberty at 28 fl oz and Reliance at 0.5 oz) and 2×rates applied singly and in combinations. This indicates that neither herbicide interacts with the Liberty Link or STS trait to predispose the stacked trait variety to the partner herbicide.

TABLE 20

| Variety | Herbicide | Application Timing | Yield* (% control) |
|---|---|---|---|
| 89248009206 | Control | — | 100.0 |
| 89248009206 | Liberty 28 fl oz | V3 | 99.5 |
| 89248009206 | Liberty 56 fl oz | V3 | 100.8 |
| 89248009206 | Reliance 25DF 0.5 oz + Poast Plus 24 fl oz | V3 | 93.7 |
| 89248009206 | Reliance 25DF 1.0 oz + Poast Plus 24 fl oz | V3 | 98.5 |
| 89248009206 | Reliance 25DF 0.5 oz + Liberty 28 fl oz | V3 | 97.9 |
| 89248009206 | Reliance 25DF 1.0 oz + Liberty 56 fl oz | V3 | 100.0 |
| 89248009206 | Reliance 25DF 0.5 oz/Liberty 28 fl oz | V3/V3 + 7da | 96.5 |
| 89248009206 | Reliance 25DF 1.0 oz/Liberty 56 fl oz | V3/V3 + 7da | 101.0 |
| 89248009206 | Liberty 28 fl oz/Reliance 25DF 0.5 oz | V3/V3 + 7da | 100.5 |
| 89248009206 | Liberty 56 fl oz/Reliance 25DF 1.0 oz | V3/V3 + 7da | 95.4 |
| 89248009206 | Liberty 105 fl oz | V3 + 7da | 94.5 |
| LSD(.10) | | | NS |
| S. E. | | | 8.3 |

*1996 means at Huxley, IA

TABLE 21

| Variety | Herbicide | Application Timing | Yield* (% control) |
|---|---|---|---|
| 89248009206 | Control | — | 100.0 |
| 89248009206 | Liberty 28 fl oz | V3 | 98.4 |
| 89248009206 | Liberty 56 fl oz | V3 | 91.9 |
| 89248009206 | Reliance 25DF 0.5 oz + Poast Plus 24 fl oz | V3 | 105.6 |
| 89248009206 | Reliance 25DF 1.0 oz + Poast Plus 24 fl oz | V3 | 100.4 |
| 89248009206 | Reliance 25DF 0.5 oz + Liberty 28 fl oz | V3 | 99.1 |

TABLE 21-continued

| Variety | Herbicide | Application Timing | Yield* (% control) |
|---|---|---|---|
| 89248009206 | Reliance 25DF 1.0 oz + Liberty 56 fl oz | V3 | 102.3 |
| 89248009206 | Reliance 25DF 0.5 oz/Liberty 28 fl oz | V3/V3 + 7da | 102.6 |
| 89248009206 | Reliance 25DF 1.0 ozlLiberty 56 fl oz | V3/V3 + 7da | 95.9 |
| 89248009206 | Liberty 28 fl oz/Reliance 25DF 0.5 oz | V3/V3 + 7da | 98.6 |
| 89248009206 | Liberty 56 fl oz/Reliance 25DF 1.0 oz | V3/V3 + 7da | 98.0 |
| 89248009206 | Liberty 105 fl oz | V3 + 7da | 95.7 |
| LSD (.10) | | | NS |
| C.V.(%) | | | 4.6 |

*1996 means at Williams, IA

Response of the LL/STS stacked trait variety to Liberty and Synchrony herbicides in 1996 are summarized in Table 22. Tolerance was exhibited to these herbicides at 1×(Liberty at 28 fl oz and Synchrony at 0.5 oz) applied singly and in combinations. This indicates that inclusion of both the Liberty Link and STS traits in soybean does not influence its tolerance to Liberty and Synchrony herbicides.

TABLE 22

| Variety | Herbicide | Application Timing | Yield* (% control) |
|---|---|---|---|
| 89248009206 | Control | — | 100.0 |
| 89248009206 | Liberty 28 fl oz | V3 | 100.1 |
| 89248009206 | Liberty 56 fl oz | V3 | 96.6 |
| 89248009206 | Synchrony 42DF 0.5 oz + Poast Plus 24 fl oz | V3 | 99.5 |
| 89248009206 | Synchrony 42DF 1.0 oz + Poast Plus 24 fl oz | V3 | 99.1 |
| 89248009206 | Synchrony 42DF 0.5 oz + Liberty 28 fl oz | V3 | 100.3 |
| 89248009206 | Synchrony 42DF 1.0 oz + Liberty 56 fl oz | V3 | 99.1 |
| 89248009206 | Synchrony 42DF 0.5 oz/Liberty 28 fl oz | V3/V3 + 7da | 99.7 |
| 89248009206 | Synchrony 42DF 1.0 oz/Liberty 56 fl oz | V3/V3 + 7da | 92.8 |
| 89248009206 | Liberty 28 fl oz/Synchrony 42DF 0.5 oz | V3/V3 + 7da | 100.3 |
| 89248009206 | Liberty 56 fl oz/Synchrony 42DF 1.0 oz | V3/V3 + 7da | 96.5 |
| 89248009206 | Liberty 105 fl oz | V3 + 7da | 91.9 |
| LSD (.10) | | | 3.3 |
| C.V. (%) | | | 5.4 |

*1996 means across three locations (Towanda, IL; Tuscola, IL; and Atlantic, IA)

Example 13

A2704 was derived through conventional breeding methodology with ALS resistance (STS) as one of the primary selection schemes. A2704 is a widely adapted late maturity group II variety.

Subsequently, a backcrossing scheme was initiated to stack (RR) glyphosate resistance with the STS trait. Backcrossing is the act of introgressing a new trait into an adapted genotype. The resulting new genotype will almost be genetically identical to the adapted cultivar of choice except for the exception of the newly introgressed trait. Additionally, glufosinate resistance was directly transformed into A2704 creating a STS/LL resistant genotype. Subsequently, A2704STS/RR was crossed to A2704 STS/LL to derive A2704 STS/RR/LL genotypes.

Example 14

Additional combinations of two or more herbicide traits, including resistance to isoxoflutole and atrazine herbicides, may be developed by many breeding schemes coupled with biotechnology approaches. A skilled artisan knows how to develop commercially acceptable varieties in using various methods including: Identifying parents, one with one or more herbicide resistance traits and crossing this parent to another parent with one or more herbicide resistance traits.

During the development of the base population and evaluation of individual plants, more traits than the herbicide resistance traits can be selected. In order to combine herbicide resistant traits into a high yielding, agronomicaly fit cultivar, it is preferred to first develop a high yielding, agronomically fit cultivar with one herbicide resistance trait. Once this cultivar is identified, additional herbicide resistance traits can be combined through traditional backcrossing and recurrent selection schemes with other elite cultivars.

A further extension of combining herbicide resistant traits would be the direct transformation of one or more herbicide resistant genes into a high yielding, agronomically fit cultivar. This cultivar may or may not have an inherent herbicide resistance trait. A cultivar with multiple herbicide resistance traits can be developed independently through conventional breeding methods or biotechnology or combination of the two.

Although the foregoing invention has been described in some detail by way of illustration and example for purposes of clarity and understanding, it will be obvious that certain changes and modifications may be practiced within the scope of the invention, as limited only by the scope of the appended claims.

Deposit Information

A deposit of soybean seeds of this invention has been placed on deposit with the American Type Culture Collection (ATCC), Manassas, Virginia on the dates and with the accession numbers as listed below:

| Soybean Variety | Date Deposited | Accession Number |
| --- | --- | --- |
| 924181339 | 5/9/96 | 97555 |
| 928933959 | 5/9/96 | 97552 |
| 92417111 | 3/7/97 | 209209 |
| 93233925295 | 3/7/97 | 97916 |
| 89248009206 | 3/7/97 | 209208 |

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A soybean seed having genes for resistance to glyphosate and sulfonylurea herbicides, wherein said glyphosate gene is an EPSPS gene which confers tolerance to glyphosate, and said sulfonylurea gene is an ALS gene which confers tolerance to sulfonylurea.

2. A soybean plant produced by growing the seed of claim 1.

3. Pollen of the plant of claim 2.

4. Ovule or ovules of the plant of claim 2.

5. Tissue culture of the plant of claim 2.

6. A plant regenerated from the tissue culture of claim 5 wherein said plant comprises said EPSPS gene and said ALS gene.

7. A method to produce a hybrid seed comprising crossing a first parent plant with a second parent plant and harvesting the resultant $F_1$ hybrid seed, wherein said first or second parent plant is the plant of claim 2.

8. A first generation ($F_1$) hybrid plant produced by growing said hybrid seed of claim 7 wherein said first generation hybrid plant comprises said EPSPS gene and said ALS gene.

9. Progeny of the plant of claim 8 wherein said progeny plant comprises said EPSPS gene and said ALS gene.

10. The soybean seed of claim 1, wherein said glyphosate gene is CP4.

11. The soybean seed of claim 1, wherein said ALS gene is derived from W20.

12. The soybean seed of claim 1, wherein said seed is capable of producing a commercially acceptable soybean plant.

* * * * *